United States Patent [19]

Johnston et al.

[11] Patent Number: 4,882,322

[45] Date of Patent: Nov. 21, 1989

[54] 3β,17β-HYDROXY-SUBSTITUTED STEROIDS AND RELATED STEROIDAL COMPOUNDS

[75] Inventors: J. O'Neal Johnston, Milford; Gene W. Holbert, Loveland, both of Ohio

[73] Assignee: Merrell Dow Pharmaceuticals Inc., Cincinnati, Ohio

[21] Appl. No.: 263,091

[22] Filed: Oct. 27, 1988

[51] Int. Cl.$^4$ ............................ A61K 31/56; C07J 1/00
[52] U.S. Cl. ....................................... 514/178; 514/182; 260/397.4; 260/397.5
[58] Field of Search ............................... 514/178, 182; 260/397.4, 397.5

[56] References Cited

U.S. PATENT DOCUMENTS 4,322,416  3/1982  Metcalf et al. .................. 260/397.3

OTHER PUBLICATIONS

J. O. Johnston, Steroids 50/1-3 (1987).

Primary Examiner—Douglas W. Robinson
Assistant Examiner—Joseph A. Lipovsky
Attorney, Agent, or Firm—John J. Kolano

[57] ABSTRACT

The present invention is directed to a group of compounds which are 3β,17β-hydroxy steriods, and related steroidal structures. These compounds are armatase inhibitors, and thus, regulate or inhibit the conversion of androgens to estrogens. These compounds may be utilized to treat conditions potentiated by the presence of estrogens. These compounds exhibit a slower onset of action and a longer half life relative to the 10-(2-alkynyl) steroidal aromatase inhibitors disclosed in U.S. Pat. No. 4,322,416.

12 Claims, No Drawings

3β,17β-HYDROXY-SUBSTITUTED STEROIDS AND RELATED STEROIDAL COMPOUNDS

BACKGROUND OF THE INVENTION

The female sex hormones estrone and estradiol are involved in many physiological processes. The formation of these steroids is regulated by a number of enzymes. The enzyme aromatase is the rate limiting enzyme in the non-reversible conversion of androgens (the hormones testosterone and androstenedione) to estrogens (the hormones estradiol and estrone). Materials such as aromatase inhibitors regulate or inhibit androgen to estrogen conversion, and thus have therapeutic utility in treating clinical conditions potentiated by the presence of estrogens. A further discussion of aromatase inhibitors may be found in U.S. Pat. No. 4,322,416.

SUMMARY OF THE INVENTION

The present invention relates to 3β,17β-hydroxy-substituted steroid aromatase inhibitors and related steroidal compounds having the following formula:

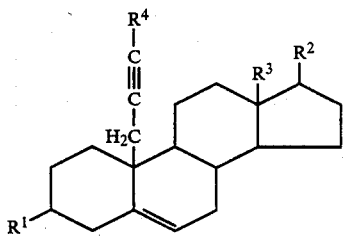

wherein:

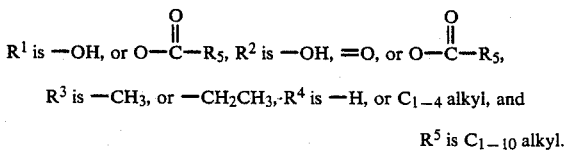

$R^3$ is —CH$_3$, or —CH$_2$CH$_3$, $R^4$ is —H, or C$_{1-4}$ alkyl, and $R^5$ is C$_{1-10}$ alkyl.

DETAILED DESCRIPTION OF THE INVENTION

The preferred compounds of the present invention are those wherein:
$R^1$ is —OH,
$R^2$ is —OH, or =O,
$R^3$ is —CH$_3$, and
$R^4$ is —H.

Some specific and representative compounds according to the invention include, but are not limited to the following compounds:
(a) 10-(2-propynyl)-19-norandrost-5-ene-3β,17β-diol, and
(b) 3β-hydroxy-10-(2-propynyl)-19-norandrost-5-ene-17-one.

The compounds of the present invention are optically active. The stereochemistry at the ring junctions is the same as that observed in the natural androstane series. Thus, the configuration of the alkynyl group is β, as are the angular hydrogen at C-8 and the angular substituent at C-13. In the compounds comprising this invention, the B/C and C/D ring junctions are trans. While the compounds having the natural steroid configuration are the active aromatase inhibitors, mixtures of these compounds with their optical antipodes are also included within the scope of the invention.

The compounds of the present invention are inhibitors of aromatase. As such, they are useful in treating hyperestrogenemia. The compounds are useful in controlling abnormally high levels of estrogens, both when the high levels observed are relatively steady, or when there are brief surges of elevated estrogen levels occurring as part of cyclical body functions. Both females and males can be treated, although obviously, the level of estrogen which would be considered high in males would be much lower than the amount considered high in females.

These compounds are also useful as anti-fertility agents to prevent ovulation or implantation in females, or to reduce the mating behavior in males where brain aromatization is required for such behavior. These compounds further have value in treating gynecomastia, male infertility resulting from elevated estrogen levels, and hyperestrogenemia, which may precede myocardial infarction. The compounds may also have value in the treatment of estrogen-dependent disease processes. The term treatment also encompasses use in the prevention of the disease processes in question. The disease processes include various estrogen-induced and estrogen-stimulated tumors such as breast, pancreatic, endometrial or ovarian cancers as well as prostate hyperplasia and benign breast disease.

The aromatase inhibitory action of the compounds of the present invention may be determined using a radioenzymatic assay. An aromatase enzyme preparation is employed from the microsomal fraction isolated from human placenta. Stereospecific elimination of 1β and 2β tritium labels from androgen substrates such as testosterone or androstenedione, and the subsequent appearance of tritated water, is utilized to measure the rate of enzyme reaction during in vitro incubations.

In evaluating the inhibition of aromatase activity, the compounds of the present invention were tested according to the folowing procedure adapted from Johnston et al., *J Steroid Biochem.*, Vol. 20, No. 6A, 1221 (1984) and Johnston, *Steroids,* Vol. 50, No. 1-3, 105 (1987). Athymic nude mice were subcutaneously injected with 1.5×10$^6$ human choriocarcinoma trophoblast (JAr) cells, which develop tumor masses of about 1 g in 10 days. Tumor aromatase activity was determined in vitro by measuring the $^3$H$_2$O resulting from the stereospecific release of 1-β $^3$H from 1-[$^3$H]-androstenedione. Cytosol (800×g) from 35 mg of tumor was the source for both aromatase and 3β-steroid dehydrogenase (SDH):isomerase activity. The test compounds were incubated for varying intervals (0–3 hrs) with aromatase prior to the addition of 34 pmol 1-[3H]-androstenedione to start a 30 min aromatase activity assay. When 10-(2-propynyl)-19-norandrost-5-ene-3β,17β-diol was tested in vitro by this procedure the following results were observed:

| | | Time-dependent JAr Tumor Aromatase Activity | | | |
|---|---|---|---|---|---|
| | | Relative Percent Inhibition | | | |
| | Conc. | Preincubation Time (hr) | | | |
| Compound | (μM) | 0 | 1 | 2 | 3 |
| 10-(2-propynyl)-19-norandrost-5-ene-3β,17β-diol | 5 | 15.1 | 0.0 | 66.9 | 71.9 |
| 10-(2-propynyl)-19-norandrost-5-ene-3β,17β-diol | 25 | 33.4 | 0.0 | 86.5 | 84.9 |

The biphase response observed suggests the decrease of the initial competitive aromatase inhibition was the result of enzymatic processing of 10-(2-propynyl)-19-norandrost-5-ene-3β,17β-diol to a more reactive component which produced a time-dependent inhibition of aromatase.

The compound 10-(2-propynyl)-19-norandrost-5-ene-3β,17β-diol was also evaluated in vivo by treating nude mice with trophoblast tumors. At 6 hr post-treatment intervals, tumor aromatase activity was determined in an in vitro assay as discussed above. The vehicle for oral dosing was PEG-200.

| Compound | In Vivo Inhibition of Aromatase Activity of JAr Tumor Xenografts in Nude Mice | | | |
|---|---|---|---|---|
| | Dose (mg/kg) | Route | No. of Mice | Relative % Inhibition 6 hr Post-treatment |
| 10-(2-propynyl)-19-norandrost-5-ene-3β,17β-diol | 7 | oral | 6 | 5.9 ± 3.0 |
| 10-(2-propynyl)-19-norandrost-5-ene-3β,17β-diol | 10 | oral | 6 | 27.5 ± 1.5 |
| 10-(2-propynyl)-19-norandrost-5-ene-3β,17β-diol | 30 | oral | 6 | 53.4 ± 7.8 |

This response indicates an increase in aromatase inhibitory activity as the dose of the compound was increased.

In the treatment of hyperestrogenemia, the compounds of the present invention may be administered in various manners to the patient being treated to achieve the desired effect. As used herein in the treatment of hyperestrogenemia, the term "patient" is taken to mean mammals, such as primates, including humans, dogs, and rodents. The compounds may be administered alone, in combination with one another, or in combination with other hormone receptor antagonists. Also, the compounds may be administered in the form of a pharmaceutical preparation.

The compounds may be administered orally or parenterally, for example, intravenously, intraperitoneally, intramuscularly, or subcutaneously, including the injection of the active ingredient directly into tissue or tumor sites such as the mammary gland. The compound may also be administered incorporated into sustained delivery devices. The amount of compound administered will vary over a wide range and be any effective amount. Depending on the patient to be treated, the condition being treated, and the mode of administration, the effective amount of compound administered will vary from about 1 to 1000 mg/kg of body weight per day, and preferably from about 40 to 200 mg/kg body weight per day.

For parenteral administration, the compounds may be administered as injectable dosages of a solution or suspension of the compound in a physiologically-acceptable diluent, with a pharmaceutical carrier, which may be a sterile liquid, such as water-in-oil, with or without the addition of a surfactant and other pharmaceutically acceptable adjuvants. Illustrative of the oils employed in these preparations are those of petroleum, animal, vegetable, or synthetic origin, for example, peanut oil, soybean oil, and mineral oil. In general, water, saline, aqueous dextrose and related sugar solutions, and ethanols and glycols, such as propylene glycol or polyethylene glycol, are the preferred liquid carriers, particularly for injectable solutions.

The compounds of the present invention exhibit a slower onset of action and a longer half life relative to the 10-(2-alkynyl) steroidal aromatase inhibitors disclosed in U.S. Pat. No. 4,322,416. Thus, these compounds may be administered in the form of a depot injection or implant. These preparations are formulated in a manner to permit the sustained release of the active ingredient. The active ingredient can also be compressed into pellets or small cylinders, and implanted subcutaneously or intramuscularly as depot injections or implants. Implants may employ inert materials, such as biodegradable polymers and synthetic silicones, for example, Silastic ®, silicone rubber manufactured by the Dow-Corning Corporation. Suitable pharmaceutical carriers and formulation techniques are found in standard texts, such as *Remington's Pharmaceutical Sciences,* Mack Publishing Company, Eaton, Pa.

The compounds of this invention may be prepared from a known compound, 3,3,17,17-bis(ethylenedioxy)-10-(2-propynyl)-19-norandrost-5-ene. This starting compound is dissolved in acetic acid, heated, treated with water, poured into a NaHCO$_3$ solution, and extracted to yield a mixture of 3,3-ethylenedioxy-10-(2-propynyl)-19-norandrost-5-en-17-one and 10-(2-propynyl)-19-norandrost-5-en-3,17-dione. This diketone is dissolved in ethanol, treated with a borohydride reducing agent to yield the 3β,17β-dihydroxy compound of the present invention.

The 17-keto compound may be prepared by treating a solution of the 3,3,17,17-bis(ethylenedioxy)-10-(2-propynyl)-19-norandrost-5-ene with a catalytic amount of an acid, such as perchloric acid. The 17-keto compound obtained is reduced with a borohydride, reducing agent, such as sodium borohydride, to yield a 17-alcohol. This compound is protected as its acetate by standard methods to yield a 17-acetoxy compound. The 17-acetoxy compound is dissolved in acetic acid, heated, treated with H$_2$O, poured into a NaHCO$_3$ solution, and extracted to afford 17-acetoxy-10-(2-propynyl)-19-norandrost-5-ene-3-one. This deconjugated ketone is subject to borohydride reduction to yield the 3-ol compound. The 3-ol is converted to the corresponding t-butyldimethyl silyl ether by standard procedures. This compound is subjected to basic hydrolysis or treated with an alkyl lithium or Grignard reagent to produce 3-t-butyldimethylsilyoxy-10-(2-propynyl)-19-norandrost-5-ene-17-ol, which is then oxidized to afford the compound 3β-hydroxy-10-(2-propynyl)-19-norandrost-5-ene-17-one.

The esters of 10-(2-propynyl)-19-norandrost-5-ene-3β,17β-diol may be prepared by reacting the above diol with an appropriate acid chloride or anhydride with or without an added solvent (i.e., CH$_2$Cl$_2$). This reaction is optionally treated with a catalytic amount of 4-dimethylaminopyridine. Thus, for example, the reaction of 10-(2-propynyl)-19-norandrost-5-ene-3β,17β-diol with acetic anhydride gives 10-(2-propynyl)-19-norandrost-5-ene-3β,17β-diacetate.

5

Employing the foregoing description, it is believed one skilled in the art can utilize the present invention to its fullest extent. The following specific examples are therefore to be construed as merely illustrative, and not limitative of the disclosure in any way.

EXAMPLE 1

A suspension of 3,3,17,17-bis(ethylenedioxy)-10-(2-propynyl)-19-norandrost-5-ene (1.3 grams) in glacial acetic acid (13 ml) was placed in a 65° C. oil bath and stirred until the steroid was dissolved. Water (3.3 ml) was added and the mixture was stirred for 8 minutes, after which time, the solution was poured into an ice-cold $NaHCO_3$ soution. The resulting product was extracted into ether. The extract was washed with bicarbonate and brine, and dried over $MgSO_4$. After filtration and concentration, the residue was chromatographed on silica gel, eluting with 40% ethyl acetate in hexane, to yield 0.69 grams of a mixture of 3,3-ethylenedioxy-10-(2-propynyl)-19-norandrost-5-en-17-one and 10-(2-propynyl)-19-norandrost-5-ene-3,17-dione.

Without further purification, the above diketone was dissolved in absolute ethanol (30 ml), treated with $NaBH_4$ (0.074 grams), and stirred for 30 minutes at room temperature. Some precipitation occurred and THF (20 ml) was added. After an additional 2.5 hours stirring, acetic acid (0.5 ml) was added and the solution was concentrated. The residue was taken up in a mixture of ether and ethyl acetate, washed with water, saturated $NaHCO_3$, and brine, and dried over $MgSO_4$. After filtration and concentration, the residue was twice subjected to silica gel chromatography, first eluting with 50% ethyl acetate in hexane, and then with 5% $CH_3OH$ in $CH_2Cl_2$, to yield 10-(2-propynyl)-19-norandrost-5-ene-3$\beta$,17$\beta$-diol (0.21 grams). Melting point 164°–166° C.

EXAMPLE 2

A solution of 3,3,17,17-bis(ethylenedioxy)-10-(2-propynyl)-19-norandrost-5-ene in a mixture of t-butanol and dichloromethane is treated with 0.3% of perchloric acid, and the solution is heated at reflux for 2 hours. After cooling to room temperature, the mixture is poured into saturated sodium carbonate solution and extracted into ether. The extract is washed with $H_2O$ and brine, dried over $MgSO_4$, filtered and concentrated to afford 3,3-ethylenedioxy-10-(2-propynyl)-19-norandrost-5-en-17-one. Analytically pure material may be obtained upon recrystallization from ethyl acetate. The 17-keto compound obtained is dissolved in ethanol and treated with sodium borohydride to produce 3,3-ethylenedioxy-10-(2-propynyl)-19-norandrost-5-en-17-ol.

The 17-alcohol obtained is protected as its acetate by standard methods. The resulting 17-acetoxy-3,3-ethylenedioxy-10-(2-propynyl)-19-norandrost-5-ene is dissolved in glacial acetic acid, heated to 65°, and treated with water. After 8 minutes, the solution is poured into ice cold saturated $NaHCO_3$, and extracted into ether. The extract is washed with $H_2O$ and brine, dried over $MgSO_4$, filtered, and concentrated. The residue is subjected to silica gel chromatography to afford 17-acetoxy-10-(2-propynyl)-19-norandrost-5-ene-3-one.

The deconjugated ketone obtained is subjected to sodium borohydride reduction to produce 17-acetoxy-10-(2-propynyl)-19-norandrost-5-en-3-ol. The 3-ol is converted to the corresponding t-butyldimethyl silyl ether by standard procedures. The 17-alcohol is unmasked either by basic hydrolysis, or treatment with an appropriate alkyl lithium or Grignard reagent, to produce 3-(t-butyldimethylsilyloxy-10-(2-propynyl)-19-norandrost-5-en-17-ol. This material is subjected to the Swern oxidation procedure, and the silyl ether protecting group is removed to afford 3$\beta$-hydroxy-10-(2-propynyl)-19-norandrost-5-en-17-one.

EXAMPLE 3

When 3,3,17,17-bis(ethylenedioxy)-10(2-butynyl)-19-norandrost-5-ene and 3,3,17,17-bis(ethylenedioxy)-18-methyl-10-(2-propynyl)-19-norandrost-5-ene are reacted according to the procedure described in Example 1, the products obtained are 10-(2-butynyl)-19-norandrost-5-ene-3$\beta$,17$\beta$-diol and 10-(2-propynyl)-18-methyl-19-norandrost-5-ene-3$\beta$,17$\beta$-diol, respectively.

What is claimed is:

1. A compound having the following formula:

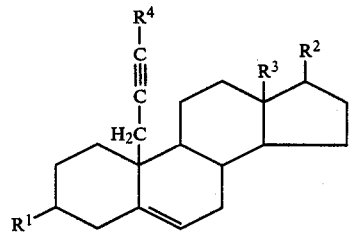

wherein:

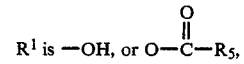

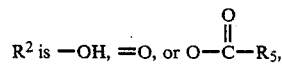

$R^3$ is $-CH_3$, or $-CH_2CH_3$, $R^4$ is $-H$, or $C_{1-4}$ alkyl, and $R^5$ is $C_{1-10}$ alkyl.

2. The compounds of claim 1 wherein $R^3$ is $-CH_3$.

3. The compounds of claim 2 wherein $R^4$ is H.

4. The compounds of claim 3 wherein $R^1$ is $-OH$.

5. The compounds of claim 3 wherein $R^2$ is $-OH$.

6. 10-(2-Propynyl)-19-norandrost-5-ene-3$\beta$,17$\beta$-diol, a compound of claim 1.

7. 3$\beta$-Hydroxy-10-(2-propynyl)-19-norandrost-5-ene-17-one, a compound of claim 1.

8. A method of inhibiting aromatase activity, which comprises exposing an effective aromatase-inhibiting amount of a compound of claim 1 with a 3$\beta$-hydroxysteroid dehydrogenase-isomerase and aromatase enzyme.

9. A method according to claim 8 in which the aromatase inhibition produces an anti-fertility effect.

10. A method of treating hyperestrogenemia, which comprises administering to a patient having said condition an effective aromatase-inhibiting amount of a compound of claim 1.

11. A method of treating estrogen-dependent disease processes which comprises administering to a patient having such a condition an effective aromatase-inhibiting amount of a compound of claim 1.

12. A process for preparing a compound of the formula

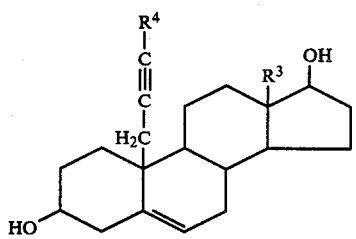
wherein R₃ is —CH₃ or —CH₂CH₃, and
R₄ is —H or $C_{1-4}$ alkyl
which comprises reacting a compound of the formula
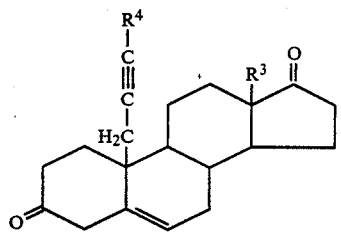
with sodium borohydride.
* * * * *

UNITED STATES PATENT AND TRADEMARK OFFICE
CERTIFICATE OF CORRECTION

PATENT NO. : 4,882,322
DATED : November 21, 1989
INVENTOR(S) : J. O'Neal Johnston, et al.

It is certified that error appears in the above-identified patent and that said Letters Patent is hereby corrected as shown below:

Column 3, Line 16 under dose patent reads: "7" and should read: --1--.

Column 5, Line 62 patent reads "-5-ene-3" and should read: ---5-en-3--.

In the Abstract, Line 3 patent reads "armatase" and should read: --aromatase--.

Signed and Sealed this

Twenty-fourth Day of September, 1991

Attest:

HARRY F. MANBECK, JR.

*Attesting Officer*     *Commissioner of Patents and Trademarks*